(12) United States Patent
Wickstrom

(10) Patent No.: US 9,999,692 B2
(45) Date of Patent: Jun. 19, 2018

(54) RADIOLABELLING PROCESS

(71) Applicant: GE Healthcare Limited, Buckinghamshire (GB)

(72) Inventor: Torild Wickstrom, Oslo (NO)

(73) Assignee: GE Healthcare Limited, Buckinghamshire (GB)

( * ) Notice: Subject to any disclaimer, the term of this patent is extended or adjusted under 35 U.S.C. 154(b) by 0 days. days.

(21) Appl. No.: 14/780,900

(22) PCT Filed: Mar. 28, 2014

(86) PCT No.: PCT/EP2014/056344
§ 371 (c)(1),
(2) Date: Sep. 28, 2015

(87) PCT Pub. No.: WO2014/154886
PCT Pub. Date: Oct. 2, 2014

(65) Prior Publication Data
US 2016/0051710 A1 Feb. 25, 2016

(30) Foreign Application Priority Data
Mar. 28, 2013 (GB) .................................. 1305687.4

(51) Int. Cl.
*A61K 51/00* (2006.01)
*A61K 51/04* (2006.01)
*C07B 59/00* (2006.01)
*C07C 51/377* (2006.01)
*C07C 61/15* (2006.01)

(52) U.S. Cl.
CPC ...... *A61K 51/0402* (2013.01); *A61K 51/0406* (2013.01); *A61K 51/0497* (2013.01); *C07B 59/001* (2013.01); *C07C 51/377* (2013.01); *C07C 61/15* (2013.01); *C07B 2200/05* (2013.01)

(58) Field of Classification Search
CPC ............ A61K 51/0402; A61K 51/0406; A61K 51/0497; C07B 59/001; C07C 51/377; C07C 61/15
USPC ....................................................... 424/1.89
See application file for complete search history.

(56) References Cited

U.S. PATENT DOCUMENTS

| 5,808,146 | A | 9/1998 | Goodman et al. |
| 7,837,982 | B2 | 11/2010 | Goodman |
| 7,910,745 | B2 | 3/2011 | Toyama et al. |
| 8,969,580 | B2 | 3/2015 | Horn et al. |
| 2013/0324715 | A1 | 12/2013 | Wickstrom |

FOREIGN PATENT DOCUMENTS

| EP | 2106808 | | 10/2009 |
| EP | 2119458 | | 11/2009 |
| EP | 1889834 | | 6/2010 |
| EP | 2230229 | A1 | 9/2010 |
| EP | 2017258 | | 3/2012 |
| EP | 2978456 | A1 | 2/2016 |
| JP | 2000500442 | A | 1/2000 |
| JP | 2008546783 | A | 12/2008 |
| RU | 2445120 | C2 | 3/2012 |
| RU | 2476423 | C2 | 2/2013 |
| WO | 199717092 | A1 | 5/1997 |
| WO | 2006126410 | A1 | 11/2006 |
| WO | 2007/001958 | A2 | 1/2007 |
| WO | 2011044410 | A2 | 4/2011 |
| WO | 2012089594 | A1 | 7/2012 |
| WO | WO 2013093025 | A1 * | 6/2013 |
| WO | 2014/154886 | A1 | 10/2014 |

OTHER PUBLICATIONS

Channing et al. Nucl. Med. Biol. 28 (2001) 469-471.*
Oh et al. Nucl. Med. Biol. 31 (2004) 803-809.*
J. A. Nye et. al.: "Biodistribution and Radiation Dosimetry of the Synthethic Nonmetabolized Amino Acid Analogue Anti-18F-FACBC in Humans", The Journal of nuclear Medicine, vol. 48, No. 6, Jun. 1, 2007.
Yu W et. al.: "Synthesis and biological evaluation of anti-1-amino-2-1-carboxylic acid in rat 9L gliosarcoma", BioOganic & Medicinal Chemistry Letters, Pergamon, Amsterdam, NL, vol. 20, No. 7, Apr. 1, 2010.
Anders Svadberg et. al: Degradation of acetonitrile in eluent solutions for [18F] fluoride PET chemistry: Impact on radiosyntheseis of [18F] FACBC and [18F] FDG, Journal of Labelled Compounds and Radiopharmaceuticals, vol. 55, No. 3, Mar. 5, 2012.
International Search Report and Written Opinion dated Jun. 25, 2014 which was issued in connection with PCT Patent Application No. EP2014/056344 which was filed on Mar. 28, 2014.
Shoup et. al: "Synthesis fo [F18]—1 amino -3- fluorocyclobutane-1-carboxylic acid (FACBC): a PET tracer for tumor delineation". , Journal of Labelled Compounds and Radiopharmaceuticals, vol. 55, No. 3, 1999.
Great Britain Search Report and Written Opinion dated Aug. 21, 2013 with was filed in connection with Great Britain Patent Application No. 1305687.4 which was filed on Mar. 28, 2013.
Office Action received for Chinese Patent Application No. 201480018669.1, dated Apr. 14, 2017, 21 pages (13 pages of English Translation + 8 pages of Official Copy).
International Preliminary Report on Patentability received for PCT Patent Application No. PCT/EP2014/056344 dated Sep. 29, 2015, 6 pages.
Office Action + Search Report Received for Russian Patent Application No. 2015138540/15, dated Feb. 28, 2018, 11 Pages (5 Pages of English Translation + 6 Pages Official Copy).
Japan Notice of Preliminary Rejection for Japanese Patent Application No. 2016-504702, dated Feb. 13, 2018, 3 pages.

* cited by examiner

*Primary Examiner* — Michael G Hartley
*Assistant Examiner* — Sean R Donohue
(74) *Attorney, Agent, or Firm* — Wood IP LLC

(57) ABSTRACT

The present invention relates to a novel composition comprising 1-amino-3-[$^{18}$F]-fluorocyclobutanecarboxylic acid ([$^{18}$F]-FACBC) wherein said composition has certain superior properties in comparison with known compositions comprising [$^{18}$F]-FACBC. Also provided by the invention is a method to obtain said composition.

18 Claims, No Drawings

RADIOLABELLING PROCESS

BACKGROUND

Technical Field of the Invention

The invention relates to a method for the preparation of a radiopharmaceutical compound, in particular an amino acid derivative useful as a positron emission tomography (PET) tracer. Embodiments of the present invention are especially suitable when automated and offers advantages over known methods. Particularly, the invention relates to a method for preparation of [$^{18}$F]-1-amino-3-fluorocyclobutane-1-carboxylic acid ([$^{18}$F]-FACBC, also known as [$^{18}$F]-fluciclovine).

Description of Related Art

The non-natural amino acid [$^{18}$F]-1-amino-3-fluorocyclobutane-1-carboxylic acid ([$^{18}$F]-FACBC, also known as [$^{18}$F]-Fluciclovine) is taken up specifically by amino acid transporters and has shown promise for tumour imaging with positron emission tomography (PET).

A known synthesis of [$^{18}$F]-FACBC (EP2017258) begins with the provision of the protected precursor compound 1-(N-(t-butoxycarbonyl)amino)-3-[((trifluoromethyl)sulfonyl)oxy]-cyclobutane-1-carboxylic acid ethyl ester. This precursor compound is first labelled with [$^{18}$F]-fluoride:

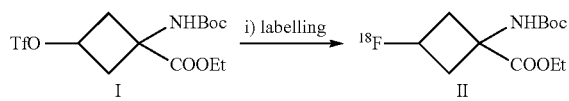

before removal of the two protecting groups:

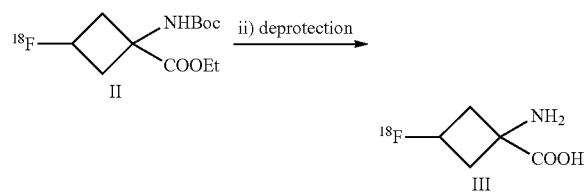

To then obtain injectable [$^{18}$F]FACBC drug product the crude [$^{18}$F]FACBC is purified and then formulated.

In the current routine process for producing [$^{18}$F]FACBC the radiolabelling step (i) is carried out in a reaction vessel followed by transfer of the radiolabelled compound of Formula II above to a tC 18 solid phase extraction column for removal of the ester protecting group by alkaline hydrolysis. During this time, the reaction vessel is washed several times with water. The ester-deprotected compound is then returned to the reaction vessel for the removal of the Boc protecting group by acid hydrolysis. Despite washing the reaction vessel several times, the present inventors have determined residual acetonitrile levels in formulated [$^{18}$F]FACBC drug /product ranging from around 100 µg/ml to around 600 µg/ml. While these levels are acceptable in terms of permitted daily exposure and in the context of the acceptance criteria for [$^{18}$F]FACBC drug product, the amount and observed variability is less than ideal.

There is therefore scope for the provision of an [$^{18}$F]FACBC drug product wherein the levels of acetonitrile are more tightly controlled, and more particularly within a lower concentration range.

SUMMARY OF THE INVENTION

Embodiments of the present invention relate to a novel composition comprising 1-amino-3-[$^{18}$F]-fluorocyclobutanecarboxylic acid ([$^{18}$F]-FACBC) wherein the composition has certain superior properties in comparison with known compositions comprising [$^{18}$F]-FACBC. In other embodiments, the present invention provides an [$^{18}$F]FACBC composition that has low and consistent amounts of residual solvent. Also provided in an embodiment of the present invention isa method to obtain the composition.

DETAILED DESCRIPTION

In one aspect the present invention relates to a composition comprising 1-amino-3-[$^{18}$F]-fluorocyclobutanecarboxylic acid ([$^{18}$F]-FACBC) wherein the composition comprises acetonitrile (MeCN) at a concentration of no greater than 50 µg/mL.

In one embodiment the composition of the present invention comprises MeCN at a concentration no greater than 20 µg/mL.

In one embodiment the composition of the present invention has a radioactive concentration (RAC) of between 500-5000 MBq/ml, more particularly between 1000-5000 MBq/ml. The RAC of the composition of an embodiment of the present invention is the RAC of the drug product as soon as this is obtained, i.e. immediately following radiofluorination, deprotection, purification and formulation.

In one embodiment the composition of the present invention has a radiochemical purity (RCP) of at least 99%.

In one embodiment the [$^{18}$F]FACBC in the composition of the present invention is trans-1-amino-3-[$^{18}$F]-fluorocyclobutanecarboxylic acid (anti-[$^{18}$F]-FACBC):

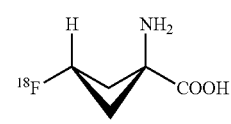

In an embodiment of the present invention, the composition is obtainable by the method of the invention described hereinbelow.

In another aspect, the present invention provides a method to obtain the composition as defined above wherein the method comprises:

(i) reacting [$^{18}$F]fluoride with a precursor compound of Formula I:

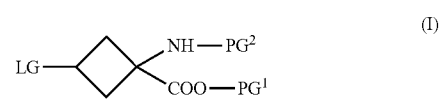

wherein:

LG is a leaving group;

PG$^1$ is carboxy protecting group; and,

PG$^2$ is an amine protecting group;

wherein the reacting step is carried out in acetonitrile;

to obtain a reaction mixture comprising a compound of Formula II:

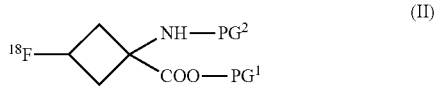

(II)

wherein:
PG$^1$ and PG$^2$ are as defined for Formula I;
(ii) transferring the compound of Formula II out of the reaction vessel to carry out removal of PG$^1$ and thereby obtain a compound of Formula III:

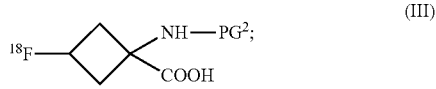

(III)

wherein PG$^2$ is as defined for Formula I;
(iii) simultaneously to step(ii) applying heat to the reaction vessel;
(iv) transferring the compound of Formula III back into the reaction vessel to carry out removal of PG$^2$ and thereby obtain [$^{18}$F]-FACBC.

A method of the invention is largely carried out as described in the art (e.g. Shoup et al 1999 J Labelled Comp Radiopharm; 42: 215-225, Svadberg et al 2011 J Labelled Comp Radiopharm; 55: 97-102) with the addition of step (iii).

The "[$^{18}$F]fluoride" suitable for use in an method of the invention is normally obtained as an aqueous solution from the nuclear reaction $^{18}$O(p,n)$^{18}$F. In order to increase the reactivity of fluoride and to reduce or minimise hydroxylated by-products resulting from the presence of water, water is removed from [$^{18}$F]-fluoride prior to the reaction, and fluorination reactions are carried out using anhydrous reaction solvents (Aigbirhio et al 1995 J Fluor Chem; 70: 279-87). A further step that is used to improve the reactivity of [$^{18}$F]-fluoride for radiofluorination reactions is to add a cationic counterion prior to the removal of water. Suitably, the counterion should possess sufficient solubility within the anhydrous reaction solvent to maintain the solubility of the [$^{18}$F]-fluoride. Therefore, counterions that are used in embodiments of the present invention include large but soft metal ions such as rubidium or caesium, potassium complexed with a cryptand such as Kryptofix™, or tetraalkylammonium salts, wherein potassium complexed with a cryptand such as Kryptofix™, or tetraalkylammonium salts.

A "precursor compound" comprises a non-radioactive derivative of a radiolabelled compound, designed so that chemical reaction with a convenient chemical form of the detectable label occurs site-specifically; can be conducted in the minimum number of steps (ideally a single step); and without the need for significant purification (ideally no further purification), to give the desired radiolabelled compound. Such precursor compounds are synthetic and can conveniently be obtained in good chemical purity.

A suitable "leaving group" in the context of the present invention is a chemical group that can be displaced by nucleophilic displacement reaction with fluoride ion. These are well-known in the art of synthetic chemistry. In some embodiments the leaving group of the present invention is a linear or branched C$_{1-10}$ haloalkyl sulfonic acid substituent, a linear or branched C$_{1-10}$ alkyl sulfonic acid substituent, a fluorosulfonic acid substituent, or an aromatic sulfonic acid substituent. In other embodiments of the invention the leaving group is selected from methanesulfonic acid, toluenesulfonic acid, nitrobenzenesulfonic acid, benzenesulfonic acid, trifluoromethanesulfonic acid, fluorosulfonic acid, and perfluoroalkylsulfonic acid. In some embodiments the leaving group is either methanesulfonic acid, trifluoromethanesulfonic acid or toluenesulfonic acid and in another embodiment the leaving group is trifluoromethanesulfonic acid.

The term "protecting group" refers to a group which inhibits or suppresses undesirable chemical reactions, but which is designed to be sufficiently reactive that it may be cleaved from the functional group in question to obtain the desired product under mild enough conditions that do not modify the rest of the molecule. Protecting groups are well known to those skilled in the art and are described in 'Protective Groups in Organic Synthesis', Theorodora W. Greene and Peter G. M. Wuts, (Fourth Edition, John Wiley & Sons, 2007).

In an embodiment of the present invention, the PG$^1$ "carboxy protecting group" is linear or branched C$_{1-10}$ alkyl chain or an aryl substituent. The term "alkyl" used either alone or as part of another group is defined as any straight, branched or cyclic, saturated or unsaturated C$_n$H$_{2n+1}$ group. The term "aryl" refers to any C$_{6-14}$ molecular fragment or group which is derived from a monocyclic or polycyclic aromatic hydrocarbon, or a monocyclic or polycyclic heteroaromatic hydrocarbon. In one embodiment of the invention PG$^1$ is selected from methyl, ethyl, t-butyl and phenyl. In another embodiment of the invention PG$^1$ is methyl or ethyl and in yet another embodiment PG$^1$ is ethyl.

The PG$^2$ "amine protecting group" suitably prevents reaction between $^{18}$F and the amino group in the process of providing the compound of Formula II. Examples of suitable amine protecting groups include various carbamate substituents, various amide substituents, various imide substituents, and various amine substituents. In an embodiment, the amine protecting group is selected from the group consisting of linear or branched C$_{2-7}$ alkyloxycarbonyl substituents, linear or branched C$_{3-7}$ alkenyloxycarbonyl substituents, C$_{7-12}$ benzyloxycarbonyl substituents that may have a modifying group, C$_{2-7}$ alkyldithiooxycarbonyl substituents, linear or branched C$_{1-6}$ alkylamide substituents, linear or branched C$_{2-6}$ alkenylamide substituents, C$_{6-11}$ benzamide substituents that may have a modifying group, C$_{4-10}$ cyclic imide substituents, C$_{6-11}$ aromatic imine substituents that may have a substituent, linear or branched C$_{i-6}$ alkylamine substituents, linear or branched C$_{2-6}$ alkenylamine substituents, and C$_{6-11}$ benzylamine substituents that may have a modifying group. In some embodiments of the invention PG$^2$ is selected from t-butoxycarbonyl, allyloxycarbonyl, phthalimide, and N-benzylideneamine. In other embodiments PG$^2$ is selected from t-butoxycarbonyl or phthalimide. In one embodiment of the invention PG$^2$ is t-butoxycarbonyl.

The term "reacting" refers to bringing two or more chemical substances (typically referred to in the art as "reactants" or "reagents") together to result in a chemical change in one or both/all of the chemical substances.

The "removal of PG$^1$" is carried out using a reagent capable of removing the carboxy protecting group PG$^1$ from the compound of Formula II during step (ii) of a method of the invention. Suitable such carboxy deprotecting agents are well-known to the skilled person (see Greene and Wuts, supra) and may be either an acid or an alkaline solution. The concentration of the PG$^1$ deprotecting agent is not limited as long as it is sufficient to remove the carboxy protecting group PG$^1$ and does not have an effect on the final purity or results in an incompatibility with any container used. In an embodiment the PG$^1$ deprotecting agent is an alkaline solution. In certain embodiments the $PG^1$ deprotecting agent is a sodium hydroxide or a potassium hydroxide solution and in another embodiment is a sodium hydroxide solution, for example of 0.5-2.0M. The reacting step is enabled by closing the outlet of the SPE column so that the $PG^1$ deprotecting agent is retained therein for a specified amount of time. The temperature and the duration of this reacting step need to be sufficient to permit removal of the $PG^1$ carboxy deprotecting group. In certain embodiments the reacting step is carried out at room temperature and for a duration of between 1-5 minutes.

Step (iii) comprises applying heat to the reaction vessel, which may be carried out using methods well-known to the person skilled in the art and must be suitable for application to the reaction vessel so that the reaction vessel may be used for the subsequent step (iv). This step (iii) is carried out "simultaneously" to step (ii), which is to say at the same time as the carrying out removal of $PG^1$, i.e. after the compound of Formula II has been transferred out of the reaction vessel. A suitable temperature for this heating step should be no greater than the tolerance of the reaction vessel, e.g. for a reaction vessel made from cyclic olefin copolymer (COC) a temperature of no greater than about 130° C. and for a reaction vessel made from polyetheretherketone (PEEK) a temperature of no greater than about 200° C. For convenience, the temperature used to heat the reaction vessel in step (iii) may be as close as possible to the temperature used during the labelling step (i). For radiolablling suitable temperatures that are used are in the range of about 80-140° C., in other cases 85-130° C.

The "removal of $PG^2$" is carried out with a reagent capable of removing the amine protecting group $PG^2$ from the compound of Formula III during the step (iv) of a method of the invention. Suitable such amine deprotecting agents are well-known to the skilled person (see Greene and Wuts, supra) and may be either an acid or an alkaline solution. The concentration of the $PG^2$ deprotecting agent is not limited as long as it is sufficient to remove the carboxy protecting group $PG^2$. In an embodiment, the $PG^2$ deprotecting agent is an acid solution. A suitable acid more particularly includes an acid selected from inorganic acids such as hydrochloric acid, sulfuric acid and nitric acid, and organic acids such as perfluoroalkyl carboxylic acid, e.g. trifluoroacetic acid. In certain embodiments, the $PG^2$ deprotecting agent is hydrochloric acid, and in other embodiments when HCl is used as $PG^2$ deprotecting agent it is at a concentration of 1.0-4.0M. Step (iv) in an embodiment is carried out with heat to allow the removal of $PG^2$ reaction to proceed more rapidly. The reaction time depends on the reaction temperature or other conditions. For example, when step (iv) is performed at 60° C., a sufficient reaction time is 5 minutes.

Precursor compounds of Formula I may be obtained by following or adapting methods known in the art, such as for example described by McConathy et al (2003 Appl Radiat Isotop; 58: 657-666) or by Shoup and Goodman (1999 J Label Comp Radiopharm; 42: 215-225).

In an aspect, the $[^{18}F]$-FACBC is trans-1-amino-3-$[^{18}F]$-fluorocyclobutanecarboxylic acid (anti-$[^{18}F]$-FACBC):

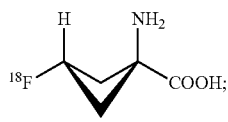

the compound of Formula I is a compound of Formula Ia:

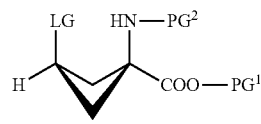

the compound of Formula II is a compound of Formula IIa:

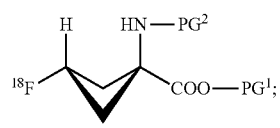

and, the compound of Formula III is a compound of Formula IIIa:

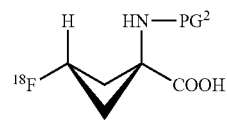

wherein $PG^1$ and $PG^2$ are as described hereinabove.

In one embodiment, a method of the present invention is automated. More particularly, the method in an embodiment of the present invention is carried out on an automated synthesis apparatus. By the term "automated synthesis apparatus" is meant an automated module based on the principle of unit operations as described by Satyamurthy et al (1999 Clin Positr Imag; 2(5): 233-253). The term 'unit operations" means that complex processes are reduced to a series of simple operations or reactions, which can be applied to a range of materials. In an embodiment, automated synthesis apparatuses are used for a method of the present invention especially when there is a radiopharmaceutical composition. They are commercially available from a range of suppliers (Satyamurthy et al, above), including: GE Healthcare; CTI Inc; Ion Beam Applications S. A. (Chemin du Cyclotron 3, B-1348 Louvain-La-Neuve, Belgium); Raytest (Germany) and Bioscan (USA).

A commercial automated synthesis apparatus also provides suitable containers for the liquid radioactive waste generated as a result of the radiopharmaceutical preparation. Automated synthesis apparatuses are not typically provided with radiation shielding, since they are designed to be employed in a suitably configured radioactive work cell. The radioactive work cell provides suitable radiation shielding to protect the operator from potential radiation dose, as well as ventilation to remove chemical and/or radioactive vapours. In an embodiment, the automated synthesis apparatus carries out the radiosynthesis by means of a cassette. By the term "cassette" is meant a piece of apparatus designed to fit removably and interchangeably onto an automated synthesis apparatus, in such a way that mechanical movement of moving parts of the synthesizer controls the operation of the cassette from outside the cassette, i.e. externally. Suitable cassettes comprise a linear array of valves, each linked to a port where reagents or vials can be attached, by either needle puncture of an inverted septum-sealed vial, or by gas-tight, marrying joints. Each valve has a male-female joint which interfaces with a corresponding moving arm of the automated synthesis apparatus. External rotation of the arm thus controls the opening or closing of the valve when the cassette is attached to the automated synthesis apparatus. Additional moving parts of the automated synthesis apparatus are designed to clip onto syringe plunger tips, and thus raise or depress syringe barrels.

The cassette is versatile, typically having several positions where reagents can be attached, and several suitable for attachment of syringe vials of reagents or chromatography cartridges (e.g. for SPE). The cassette always comprises a reaction vessel. In an embodiment, the reaction vessels are 0.5 to 10 mL, particularly 0.5 to 5 mL and more particularly 0.5 to 4 mL in volume and are configured such that 3 or more ports of the cassette are connected thereto, to permit transfer of reagents or solvents from various ports on the cassette. In an embodiment, the cassette has 15 to 40 valves in a linear array, particularly 20 to 30, more particularly 25. In an embodiment, the valves of the cassette are each identical, and more particularly are 3-way valves. The cassettes are designed to be suitable for radiopharmaceutical manufacture and are therefore manufactured from materials which are of pharmaceutical grade and ideally also are resistant to radiolysis.

In an embodiment, the automated synthesis apparatuses for use with the present invention comprise a disposable or single use cassette which comprises all the reagents, reaction vessels and apparatus necessary to carry out the preparation of a given batch of radiofluorinated radiopharmaceutical. The cassette means that the automated synthesis apparatus has the flexibility to be capable of making a variety of different radiopharmaceuticals with minimal risk of cross-contamination, by simply changing the cassette. The cassette approach also has the advantages of: simplified set-up hence reduced risk of operator error; improved GMP (Good Manufacturing Practice) compliance; multi-tracer capability; rapid change between production runs; pre-run automated diagnostic checking of the cassette and reagents; automated barcode cross-check of chemical reagents vs the synthesis to be carried out; reagent traceability; single-use and hence no risk of cross-contamination, tamper and abuse resistance.

The following example serves to further illustrate embodiments of the present invention.

Brief Description of the Examples

Example 1 describes a known method to obtain $[^{18}F]$ FACBC.

Example 2 describes a method to obtain $[^{18}F]$FACBC according to the present invention.

List of Abbreviations used in the Examples
BOC tert-Butyloxycarbonyl
DP drug product
HLB hydrophobic-lipophilic balance
$K_{222}$ Kryptofix 222
MeCN acetonitrile
QMA quaternary methyl ammonium
RAC radioactive concentration

EXAMPLES

Comparative Example 1

Prior Art Synthesis of $[^{18}F]$FACBC

FAST1ab Cassette.

All radiochemistry was performed on a commercially available GE FASTlab™ with single-use cassettes. Each cassette is built around a one-piece-moulded manifold with 25 three-way stopcocks, all made of polypropylene. Briefly, the cassette includes a 5 ml reactor (cyclic olefin copolymer), one 1 ml syringe and two 5 ml syringes, spikes for connection with five prefilled vials, one water bag (100 ml) as well as various SPE cartridges and filters. Fluid paths are controlled with nitrogen purging, vacuum and the three syringes. The fully automated system is designed for single-step fluorinations with cyclotron-produced $[^{18}F]$fluoride. The FAST1ab was programmed by the software package in a step-by-step time-dependent sequence of events such as moving the syringes, nitrogen purging, vacuum, and temperature regulation. Vial A contained $K_{222}$ (58.8 mg, 156 μmol), $K_2CO_3$ (8.1 mg, 60.8 μmol) in 79.5% (v/v) $MeCN_{(aq)}$(1105 μl). Vial B contained 4M HCl (2.0 ml). Vial C contained MeCN (4.1 ml). Vial D contained the precursor (48.4 mg, 123.5 μmol) in its dry form (stored at −20° C. until cassette assembly). Vial E contained 2 M NaOH (4.1 ml). The 30 ml product collection glass vial was filled with 200 mM trisodium citrate (10 ml).

Production of $[^{18}F]$Fluoride.

No-carrier-added $[^{18}F]$fluoride was produced via the $^{18}O$ $(p,n)^{18}F$ nuclear reaction on a GE PETtrace 6 cyclotron (Norwegian Cyclotron Centre, Oslo). Irradiations were performed using a dual-beam, 30 μA current on two equal Ag targets with HAVAR foils using 16.5 MeV protons. Each target contained 1.6 ml of ≥96% $[^{18}O]$ water (Marshall Isotopes). Subsequent to irradiation and delivery to a hotcell, each target was washed with $[^{16}O]$water (Merck, water for GR analysis). Aqueous $[^{18}F]$fluoride was passed through the QMA and into the $^{18}O$-$H_2O$ recovery vial. The QMA was then flushed with MeCN and sent to waste.

$[^{18}F]$Fluoride Labelling.

The trapped $[^{18}F]$fluoride was eluted into the reactor using eluent from vial A and then concentrated to dryness by azeotropic distillation with acetonitrile (vial C). MeCN was mixed with precursor in vial D from which the dissolved precursor was added to the reactor and heated to 85°.

Removal of Ester Protecting Group.

The reaction mixture was diluted with water and sent through the tC 18 cartridge. Reactor was washed with water and sent through the tC18 cartridge. The labelled intermediate, fixed on the tC 18 cartridge was washed with water, and then incubated with 2M NaOH after which the 2M NaOH was sent to waste.

Removal of BOC Protecting Group.

The labelled intermediate (without the ester group) was then eluted off the tC18 cartridge into the reactor using water. The BOC group was hydrolysed by adding 4M HCl and heating the reactor.

Purification.

The reactor content with the crude $[^{18}F]$FACBC was sent through the HLB and Alumina cartridges and into the 30 ml product vial. The HLB and Alumina cartridges were washed with water and collected in the product vial.

Formulation.

2M NaOH and water was added to the product vial, giving a purified drug product (DP) with a total volume of 26 ml.

Characterisation.

Radioactive concentration (RAC) and concentration of acetonitrile were measured in the DP.

| FASTlab Run# | RAC (MBq/ml) | MeCN in DP (μg/ml) |
| --- | --- | --- |
| 1 | 1915 | 506 |
| 2 | 1804 | 324 |
| 3 | 1950 | 302 |

-continued

| FASTlab Run# | RAC (MBq/ml) | MeCN in DP (µg/ml) |
|---|---|---|
| 4 | 1698 | 89 |
| 5 | 1570 | 596 |
| 6 | 1815 | 218 |

Example 2

Synthesis of [$^{18}$F]FACBC using Inventive Method

The method as defined in Example 1 was used except that during removal of the ester protecting group, the empty reactor was heated for 5 minutes.

| FASTlab Run# | RAC (MBq/ml) | MeCN in DP (µg/ml) |
|---|---|---|
| 1 | 3247 | 16 |
| 2 | 4190 | 16 |
| 3 | 1708 | 16 |
| 4 | 776 | 17 |

What is claimed is:

1. A method to obtain a composition comprising 1-amino-3-[$^{18}$F]-fluorocyclobutanecarboxylic acid ([$^{18}$F]-FACBC) wherein said composition comprises acetonitrile (MeCN) at a concentration of no greater than 50 µg/mL wherein said method comprises:

reacting in a reaction vessel [$^{18}$F]fluoride with a precursor compound of Formula I:

(I)

wherein:
LG is a leaving group;
PG$^1$ is carboxy protecting group; and,
PG$^2$ is an amine protecting group;
wherein said reacting step is carried out in acetonitrile;
to obtain a reaction mixture comprising a compound of Formula II:

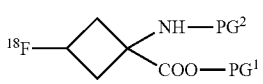

(II)

wherein:
PG$^1$ and PG$^2$ are as defined for Formula I;
transferring said compound of Formula II out of said reaction vessel onto a cartridge to leave the reaction vessel empty;
applying heat to the empty reaction vessel whilst at the same time carrying out removal of PG$^1$ and thereby obtain a compound of Formula III:

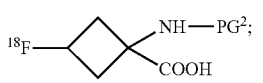

(III)

wherein PG$^2$ is as defined for Formula I; and
transferring the compound of Formula III back into said heat treated empty reaction vessel to carry out removal of PG$^2$ and thereby obtain [$^{18}$F]-FACBC.

2. The method as defined in claim 1 wherein said concentration of MeCN in said composition is no greater than 20 µg/mL.

3. The method as defined in claim 1 wherein said composition has a radioactive concentration (RAC) of between 500 - 5000 MBq/ml.

4. The method as defined in claim 3 wherein said composition has a RAC of between 1000-5000 MBq/ml.

5. The method as defined in claim 1 wherein said composition has a radiochemical purity of at least 99%.

6. The method as defined in claim 1 wherein said [$^{18}$F]FACBC is trans-1-amino-3-[$^{18}$F]-fluorocyclobutanecarboxylic acid (anti-[$^{18}$F]FACBC):

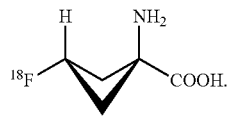

7. The method as defined claim 1 wherein LG is a linear or branched C$_{1-10}$ haloalkyl sulfonic acid substituent, a linear or branched C$_{1-10}$ alkyl sulfonic acid substituent, a fluorosulfonic acid substituent, or an aromatic sulfonic acid substituent.

8. The method as defined in claim 7 wherein LG is methanesulfonic acid, toluenesulfonic acid, nitrobenzenesulfonic acid, benzenesulfonic acid, trifluoromethanesulfonic acid, fluorosulfonic acid, or perfluoroalkylsulfonic acid.

9. The method as defined in claim 7 wherein LG is trifluoromethanesulfonic acid.

10. The method as defined in claim 1 wherein PG$^1$ is a linear or branched C$_{1-10}$ alkyl chain or an aryl substituent.

11. The method as defined in claim 10 wherein PG$^1$ is methyl, ethyl, t-butyl and phenyl.

12. The method as defined in claim 11 wherein PG$^1$ is methyl or ethyl.

13. The method as defined in claim 12 wherein PG$^1$ is ethyl.

14. The method as defined in claim 1 wherein PG$^2$ is a carbamate substituent, an amide substituent, an imide substituents, or an amine substituents.

15. The method as defined in claim 14 wherein PG$^2$ is t butoxycarbonyl, allyloxycarbonyl, phthalimide, or N-benzylideneamine.

16. The method as defined in claim 15 wherein PG$^2$ is t butoxycarbonyl.

17. The method as defined in claim 1 wherein said [$^{18}$F]FACBC is trans-1-amino-3-[$^{18}$F]-fluorocyclobutanecarboxylic acid (anti-[$^{18}$F]FACBC):

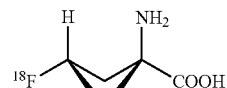

said compound of Formula I is a compound of Formula Ia:
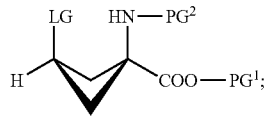
(Ia)
said compound of Formula II is a compound of Formula IIa:
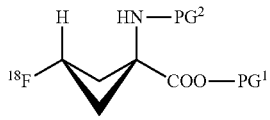
(IIa)
said compound of Formula III is a compound of Formula IIIa:
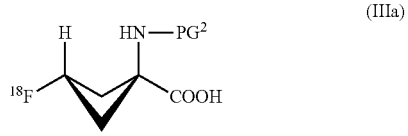
(IIIa)
wherein LG is as defined in claim 1, PG$^1$ is as defined in claim 1, and PG$^2$ is as defined in claim 1.
18. The method as defined in claim 1 which is automated.